(12) United States Patent
Mukai

(10) Patent No.: US 6,455,006 B1
(45) Date of Patent: Sep. 24, 2002

(54) APPARATUS FOR ASPIRATING AND DISCHARGING A SAMPLE QUANTITY

(75) Inventor: Hisataka Mukai, Kyoto (JP)

(73) Assignee: Kyoto Electronics Manufacturing Co., Ltd. (JP)

(*) Notice: Subject to any disclaimer, the term of this patent is extended or adjusted under 35 U.S.C. 154(b) by 0 days.

(21) Appl. No.: 09/551,696

(22) Filed: Apr. 18, 2000

(30) Foreign Application Priority Data

Apr. 20, 1999 (JP) .......................................... 11-112163

(51) Int. Cl.[7] .............................. B01L 3/02; G01H 1/10; G01H 1/16; G01H 1/26; G01H 1/14
(52) U.S. Cl. .................... 422/100; 436/180; 73/863.32; 73/864; 73/864.01; 73/864.02; 73/864.11; 73/864.13; 73/864.16; 73/864.17; 73/863.33
(58) Field of Search ................ 422/100, 99; 73/863.32, 73/864, 864.01, 864.11, 864.02, 864.13, 864.16, 863.33, 864.17; 436/180

(56) References Cited

U.S. PATENT DOCUMENTS

| | | | | |
|---|---|---|---|---|
| 4,399,712 A | * | 8/1983 | Oshikubo et al. |
| 4,760,939 A | * | 8/1988 | Ball et al. |
| 4,815,632 A | * | 3/1989 | Ball et al. |
| 4,929,428 A | * | 5/1990 | Tezuka |
| 5,213,764 A | * | 5/1993 | Kerr et al. |
| 5,330,721 A | * | 7/1994 | Tervamaki |
| 5,531,131 A | * | 7/1996 | Sabloewski |
| 5,665,601 A | * | 9/1997 | Kilmer |
| 5,789,259 A | * | 8/1998 | Wardlaw |
| 5,879,633 A | * | 3/1999 | Tervamaki et al. |
| 2002/0001544 A1 | * | 1/2002 | Hess et al. |

* cited by examiner

*Primary Examiner*—Jill Warden
*Assistant Examiner*—Brian R Gordon
(74) *Attorney, Agent, or Firm*—Ronald E. Greigg

(57) ABSTRACT

It has been hard to suck the high viscosity sample by using the syringe and to stop the suction of the sample.

A sample sucking-discharging device in the invention comprises an injector provided with a cylinder and a piston installed in the cylinder so as to move up and down; a main body for holding the cylinder of the injector; a gear or a pair of gears held in the main body so as to rotate on an axis right-angled to the moving direction of the piston; a first rack, of which one end is connected with the piston, for moving with meshing to the gear or the pair of gears; and, a second rack held in the main body so as to move in the direction opposite to or crossing with the moving direction of the first rack.

7 Claims, 13 Drawing Sheets

APPARATUS FOR ASPIRATING AND DISCHARGING A SAMPLE QUANTITY

BACKGROUND OF THE INVENTION

Technical Field

This invention relates to a more commonly known as an apparatus for aspirating and discharging device for supplying a sample into a detecting cell such as a prismatic refractometer or an oscillating densitometer, and after the measurement discharging the sample from said detecting cell. And more specially it relates to a well-manipulating sample sucking-discharging device that can suck and discharge a high viscosity sample, in which the speed of the sucking and discharging of the sample can be adjusted easily and arbitrarily, and the sucking and discharging operation can be performed with facility by one hand and need not to press a piston at the time of stopping the operation.

BACKGROUND OF THE INVENTION

In an oscillating densitometer composed of a U-shaped thin tube provided with a detecting cell called an oscillating cell, the density of a sample liquid is to be calculated according to the frequency of the oscillating cell when said cell is filled with the sample. The sample is introduced into the oscillating cell by sucking or pouring under pressure. In case there is an enough volume of the sample, the introduction continues for the specific time from the starting, and then stopped. In case there is a small volume of the sample, the sample extracted by an injector or a syringe is supplied to the oscillating cell by a sucking-discharging device, and after the measurement, it is drained away from said cell by the sucking-discharging device.

As shown in a block diagram in FIG. 12, a sample sucking-discharging device utilized for sucking and discharging a sample into the oscillating cell is composed of an injector, which comprises a cylinder $5a$ provided with a port at one end, a piston $5b$ installed in the cylinder $5a$ so as to move, and a spring $5c$ for pressing the piston $5b$ toward the bottom of the cylinder $5a$, and in which the port $5d$ of the cylinder $5a$ is connected with an oscillating cell of the oscillating densitometer, that is, a detecting cell.

When a sample is extracted by using the injector 5, an operator presses the piston $5b$ with his finger to the bottom of the cylinder $5a$, that is, a bottom dead position, and while a sample inlet of the detecting cell connected with the port is soaked into the sample, the power of his finger pressing down the piston $5b$ is gradually reduced and then the piston $5b$ pushed up by the force of the spring $5c$ sucks the sample into the cylinder $5a$.

And as shown in a block diagram in FIG. 13 the above apparatus is available for the sucking and discharging of a sample to an optical cell of the prismatic refractometer.

In the above injector 5, the force for sucking a sample into the cylinder $5a$ depends on the elastic force of the spring $5c$, so that it sometimes occurs that a high viscosity sample cannot be sucked. In order to suck up the high-viscosity sample, the spring $5c$ must be powerful. But in case of sucking a low viscosity sample such as an organic solvent, for example, the usage of the powerful spring $5c$ increases the speed of the sucking too much. As a result, the condition under exceedingly reduced pressure is generated; accordingly it may occur that the measurement is conducted under the condition that the sample includes small bubbles. Specifically, since the force of sucking a sample into a cylinder $5a$ of the injector 5 depends on the elastic force, the sucking speed cannot be meet with the sample characteristic, and the sucking time cannot be adjusted for a specific volume of sample. And in case of stopping the sucking not so as to suck the air after the sample sucking, it is necessary to stop the moving of the piston $5c$ by supporting with the finger. Those points are demerits in order to improve the manipulation of the apparatus.

There are also the same problems in case of using a syringe. In the injector not including a spring $5c$, the piston $5b$ needs to be pulled up by hand and the one-hand operation cannot be carried out. Therefore, the manipulation is worse.

The present invention can solve the above-mentioned problems and the objects of the invention are to provide a well-manipulating sample sucking-discharging device that can suck and discharge a high viscosity sample, in which the speed of the sucking and discharging of the sample can be adjusted easily and arbitrarily, the sucking and discharging operation can be performed with facility by one hand, and need not to press a piston at the time of stopping the operation.

SUMMARY OF THE INVENTION

In order to achieve the above object, the present invention presupposes a sample sucking-discharging device which comprising an injector provided with a cylinder and a piston installed in the cylinder so as to move up and down; a main body for holding the cylinder of the injector; a gear or a pair of gears held in the main body so as to rotate on an axis right-angled to the moving direction of the piston; a first rack, of which one end is connected with the piston, for moving with meshing with the gear or the pair of gears; and, a second rack held in the main body so as to move in the direction opposite to or crossing with the moving direction of the first rack while meshing with the gear or the pair of gears.

The injector may adopt a well-known product comprising a cylinder made from synthetic resin or glass, and a piston installed in the cylinder so as to move up and down. And it is also possible to make up one unit by combining the cylinder and the following main body.

The main body holds one gear or a pair of gears and the second rack other than the cylinder of the injector, and also holds the piston and the first rack via the cylinder. To stabilize the operation of the first rack, the first rack can be held directly by the main body.

The shape of the main body may be formed so as to hold the cylinder of the injector, the gear or the pair of gears and the second rack. It's preferable to consider the manipulation and the design. Specifically, the main body may be formed in a cylindrical form or an oval-cylindrical form, for example. And the material of the main body is not limited specially, but may adopt a resin, a metal, a glass and etc.

The gear or the pair of gears is held by the main body at the specific position toward the cylinder of the injector so as to rotate on an axis right-angled to the moving direction of the piston, and then may mesh with the first and the second rack.

In the invention, the main body holds the gear or the pair of gears, which includes one gear comprising a hub and plural teeth formed in a line around the hub, and a dual gear comprising a hub and plural teeth formed in two lines around the hub. In case of the former, the first and the second rack are arranged to mesh with the teeth formed in a line. And in case of the latter, the first and the second rack are arranged to mesh with the different line of the lined teeth respectively.

The kinds of the above-mentioned gears are not restricted particularly, if the gears can mesh with racks (teeth line) the weight formed in the first and the second rack, or with diagonal racks. And it is possible to use a spur gear of which the teeth in a straight line is cut in parallel with the axis, a helical gear of which the teeth line is twisted in diagonal to the axis, or a herringbone gear that two helical gears facing on the opposite direction each other adjoin on the same axis. But it is arranged in the invention that a common gear may mesh with both racks, so that the construction can be the simplest. And said construction can adopt the spur gear as a gear, therefore, there is a merit that the cost can be reduced.

When the invention adopts a pair of gears, it is arranged that the two gears be connected with each other so as to rotate synchronously in the same direction respectively, and the first and the second rack mesh with each different gear.

In the first rack of which the end is connected with the piston of the injector and which moves while meshing with the gear or the pair of gears, the axis direction of the first rack is positioned in parallel with the moving direction of the piston and so as to move in the axis direction.

It is not necessary to provide with means for guiding the move of the first rack in particular, but in order to stabilize the move of the first rack and to mesh it with the gear or the pair of gears accurately, it is preferable that guiding means for guiding the move of the first rack may be provided in the main body.

The second rack is held in the main body so as to move in the crossing direction or the reverse direction to the moving direction of the first rack while meshing with the gear or the pair of gears.

When the second rack is held in the main body so as to move in the direction reverse to the moving of the first rack while meshing with the gear or the pair of gears, a discharging button is provided at one end of the first rack that is connected at the other end with the piston, pressing the discharging button presses down the piston to the bottom of the cylinder via the first rack, and then the sample in the injector is discharged by the piston.

Also in this case, when a sucking button is provided at one end of the second rack that is the same side as the discharging button, pressing the sucking button pulls up the piston to the upper side of the cylinder via the second rack, gears, and the first rack moving in the direction reverse to the second rack, and then the sample is sucked into the injector.

When the second rack is held in the main body so as to move in the direction crossing with the moving direction of the first rack while meshing with the gear or the pair of gears, a discharging button is provided at one end of the second rack, while a sucking button is provided at the other end of the second rack, pressing the discharging button presses down the piston to the bottom of the cylinder via the second rack, the gear or the pair of gears, and the first rack; on the other hand, pressing the sucking button pulls up the piston to the upper side of the cylinder via the second rack, the gear and the first rack.

And in this case, when the apparatus comprises a gear composed of dual gear provided with teeth in a different radius formed in two lines, a gear in small radius and pitch is meshed with the first rack, and a gear in large radius and pitch is meshed with the second rack. Thereby, the operation of the first rack can become more powerful than that of the second rack, that is, it is possible to strengthen the operating power of the piston of the injector. The sucking of the more high viscosity sample becomes easy. The operation amount of the first rack gets to be less than that of the second rack. Therefore it is easy to perform the fine adjustment of the sucking speed for the sample.

By using a pair of gears in a different radius, a gear in small radius and pitch is meshed with the first rack, while a gear in large radius and pitch is meshed with the second rack, so that the same effect can be obtained.

When the second rack is held in the main body so as to move in the direction crossing with the moving direction of the first rack while meshing with the gear or the pair of the gear, the pressing of the first rack can discharge the sample out of the injector.

Specifically, in case the second rack is held in the main body so as to move in the direction crossing with the moving direction of the first rack while meshing with the gear or the pair of the gear; a discharging button is provided at one end of the first rack that is connected at the other end with a piston; and a sucking button is provided at one end of the second rack, pressing the discharging button presses down the piston to the bottom of the cylinder via the first rack; and on the other hand, pressing the sucking button pulls up the piston to the upper side of the cylinder via the second rack, the gear or the pair of gears, and the first rack.

As described above, the invention is arranged that the operation of pulling the piston from the bottom of the cylinder to the port is equivalent to the operation of pressing the second rack by finger. If the power of the finger is stronger, even in case of the high viscosity sample, it is possible to suck the sample into the cylinder. When the speed of pressing the second rack is adjusted by finger, it is possible to adjust the sucking speed or the time of the sucking for the specific volume. Since there is not a spring that presses the piston or the rack, or an elastic membrane that enlarges the capacity of the syringe, even when the hand is released from the rack at the stopping of the sucking and discharging, it does not move the first and the second rack, the gear or the pair of gears, and the piston. Therefore, it will not occur that the sample turns back to the cylinder or that the air is suck into the cylinder. It is not necessary to press the piston at the stopping of the sucking and the discharging.

And both the pressing and the pulling operations of the piston can be performed by the pressing operation of the first or the second racks, for example, while holding the cylinder of the injector by the palm, the little finger, the ring finger, and the middle finger of hand, the thumb and the forefinger perform the pressing and pulling operations of the piston. Therefore, one hand operation can perform the sucking and discharging easily.

The piston of the injector may be connected with the one end of the first rack so as to link with each other, and a transmitting means may be arranged to intervene between the piston and the first rack, such as a rod, a lever and etc. that is able to transmit the operation bi-directional. But it is preferable that in order to improve the certainty of the operation, the first rack is directly connected with the piston via a holder provided at one end of the first rack.

DETAILED DESCRIPTION

Figure 1:
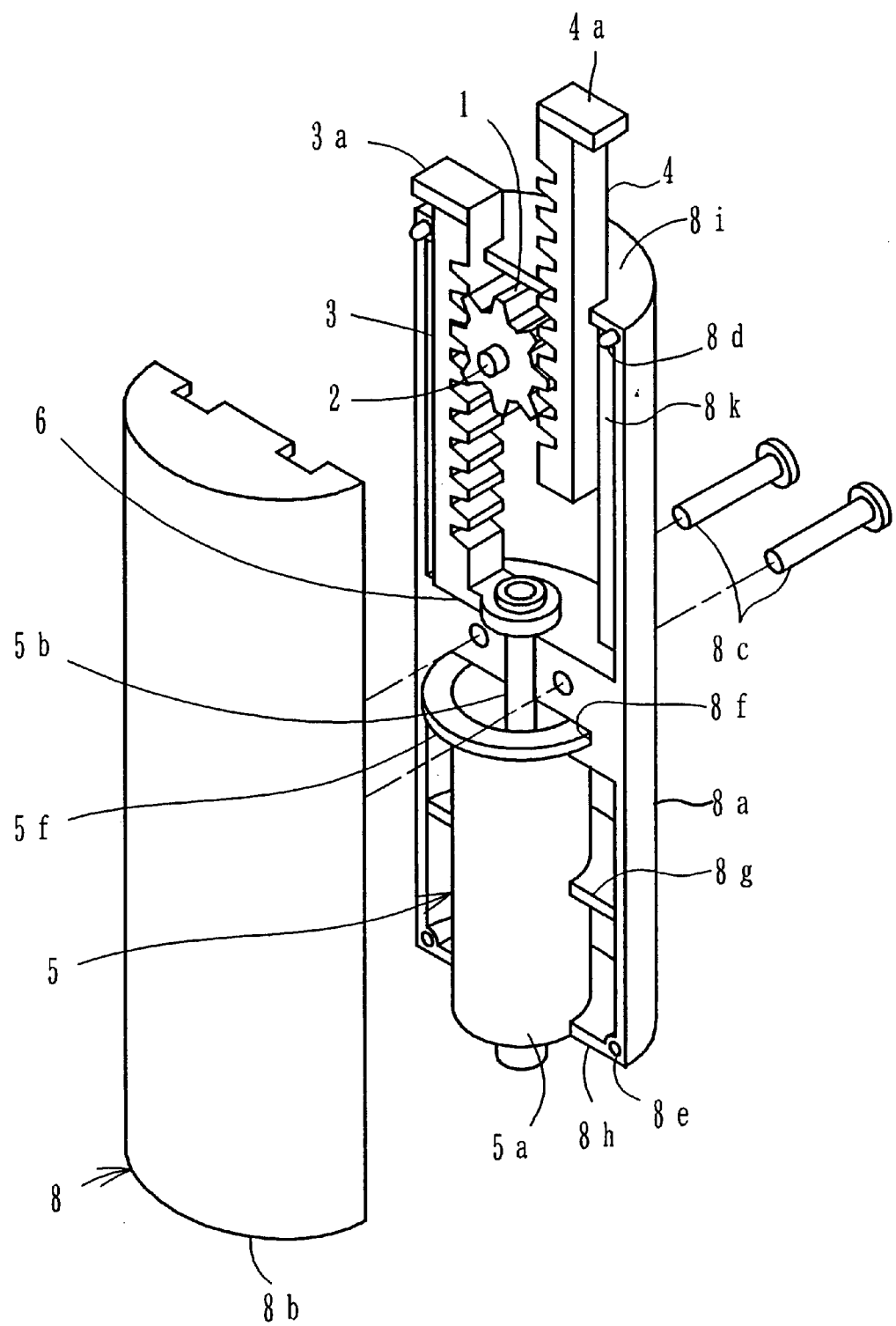
FIG. 1 is an exploded perspective view of the invention.

A sample sucking-discharging device in the first embodiment of the invention is explained hereinafter referring to the drawings.

Figure 2:
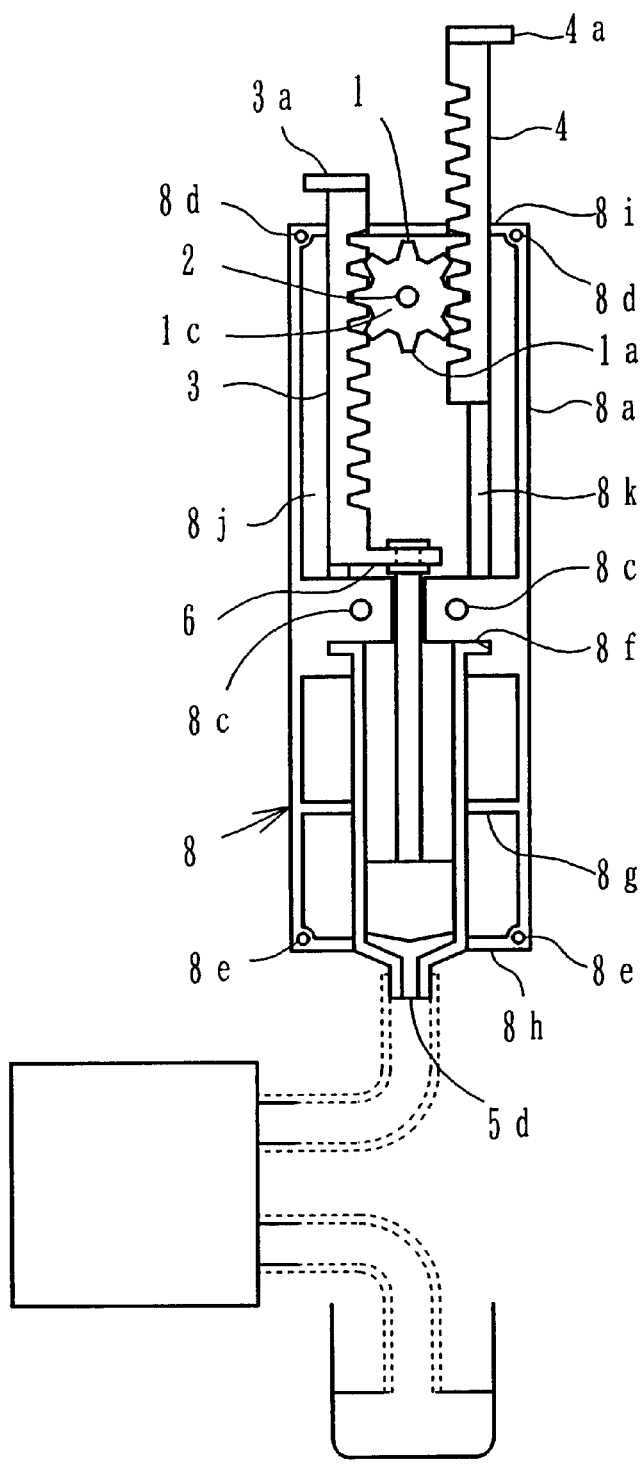
FIG. 2 is a block diagram of the invention.
Figure 3:
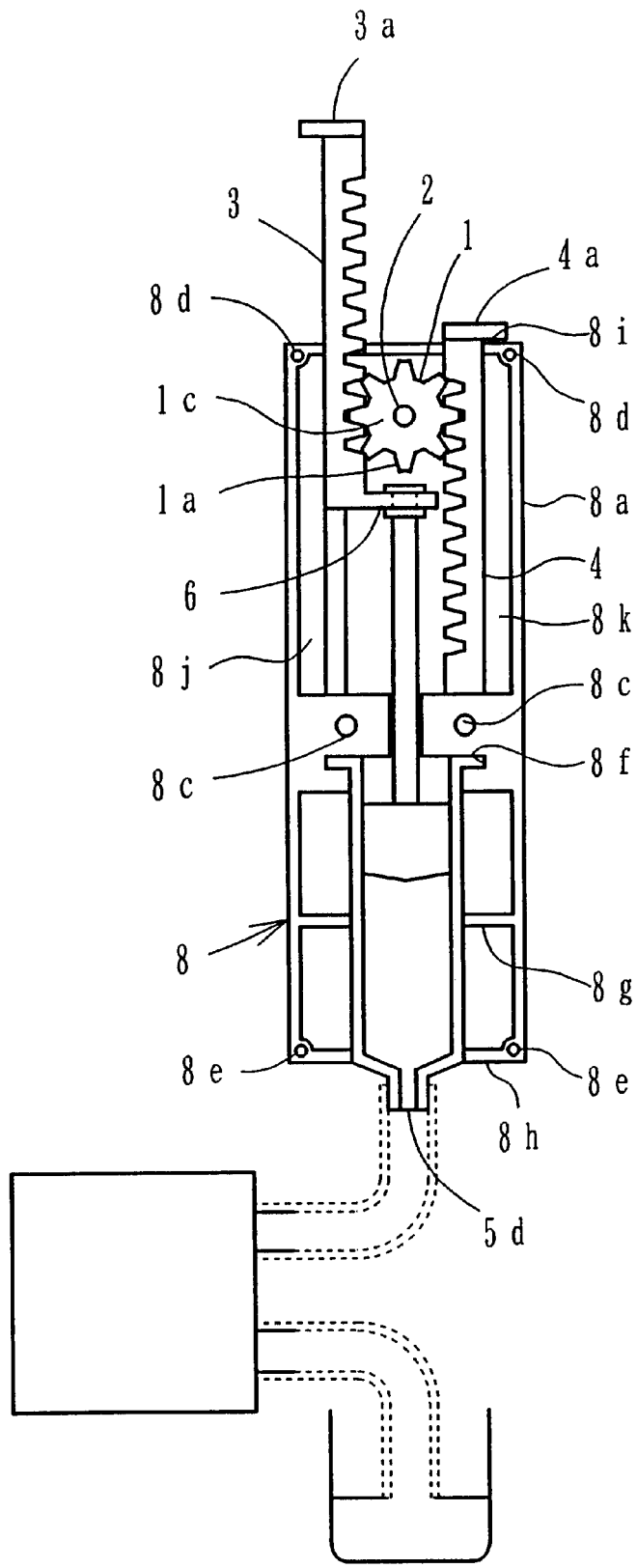
FIG. 3 is a block diagram of the invention.

FIG. 1 is an exploded perspective view of a sample sucking discharging device in the first embodiment, and FIG. 2 and FIG. 3 are block diagrams showing the outline of the apparatus schematically. The sample sucking-discharging device is provided with an injector comprising a cylinder 5a and a piston 5b installed in the cylinder 5a so as to move up and down, and a main body 8 for holding the cylinder 5a of the injector.

The main body 8 is made from resin, for example, and is formed into one unit by fitting two halves 8a and 8b opposing each other, whereby the shape is a semi-oval cylinder with closed ends. It is assembled by tightening two screws 8c going through one half 8a to the other half 8b.

At positions on both halves 8a and 8b, projections 8d and cavities 8e are formed. These opposite projections 8d and cavities 8e are engaged with each other, thereby a halves 8a and 8b fit each other.

It is needless to say that either of the halves 8a or 8b may be provided with the projection 8d. It may be arranged that the half 8a is provided with the projection 8d and the cavity 8e while the other half 8b is provided with the cavity 8e and the projection 8d opposite to the other.

The injector 5 is held in the vertical direction on the bottom of the inside of the main body 8 so that the opening of the cylinder 5a may face to down. A flange 5f of the cylinder 5a is mounted into the semicircular groove 8f formed inside the main body 8; and the rib 8g formed in the main body 8 and a bottom phase 8h in the main body receives the outside phase of the cylinder 5a. Thereby, the cylinder 5a is fixed on the specified position in the main body 8.

A shaft 2 crossing at right angles with an axis of the cylinder 5a projects from the inside phase of the half 8a, and fits together with a hub 1c and a gear comprising a spur gear provided with plural teeth formed in a line around the hub 1c so as to rotate. The top of the shaft 2 projecting from the end phase of the gear 1 fits into a cavity provided at the other half 8b that is not shown. Therefore, it is possible to avoid that the shaft vibrates and curves.

And there is arranged in the upper portion of the main body 8 that a first rack 3 moves up and down while meshing with the gear 1, and a second rack 4 is provided at the position contrasted to the first rack 3 striding over the shaft 2 so as to move up and down while meshing with the gear 1. The tops of the first rack 3 and the second rack 4 pierce through the top phase 8i respectively, and project to the upper direction.

The bottom of the first rack 3 is connected with a holder 6 projecting in right angle to the moving direction. The holder 6 is connected directly with the piston 5b. The top-end of first rack 3 projects to the upper direction of the man body 8, on which a discharging button 3a is provided.

Therefore, pressing the discharging button with grasping the main body 8 presses the piston 5b to the bottom of the cylinder 5a, and the sample is discharged from the cylinder 5a passing through the port 5d provided at the bottom of the cylinder 5a.

The first rack 3 is not necessary to be provided with means for guiding the elevation, since it is connected with the piston 5b of the injector 5. But in this embodiment, the guide portion 8j for guiding the elevation of the first rack 3 is provided so that the first rack 3 may mesh with the gear 1 steadily.

Meanwhile, the top end of the second rack 4 projects to the upper direction of the main body 8, on which a sucking button 4a is provided. And in order that the second rack 4 meshes with the gear 1 steadily, a guide portion 8k may guide the elevation of the second rack.

As shown in FIG. 2, when the sample sucking-discharging device, the piston 5b of which is positioned at the dead position, is grasped with a palm and four fingers except the thumb, and after soaking a sample inlet of the detecting cell into the sample, said detecting cell that is connected with the port 5d formed at the bottom of the cylinder 5a of the injector 5, the thumb presses down the sucking button 4a. Thereby the first rack 3 and the piston 5b are pulled up via the gear 1, and then the sample is sucked into the cylinder 5a passing through the detecting cell.

In case of the high viscosity sample, it is possible to suck the sample into the cylinder 5a by pressing down the sucking button 4a hard. And it is also possible to adjust the speed of sucking the sample into the cylinder 5a by adjusting the speed of pressing the sucking button 4a.

At the time of stopping the suction of the sample, the thumb is released from the sucking button 4a. Since the pressing operation of the second rack 4 may stop by releasing the thumb from the sucking button 4a, it is possible to avoid that the piston 5b moves by the sliding resistance of the piston 5b.

The weight difference of the first rack 3 and the second rack 4 also acts to pull up the piston 5b resisting to the weight of the piston 5b and the differential pressure moving up and down the piston 5b. And it is arranged to design the weight of the rack 3 and 4 so as to balance with the weight difference of the first rack 3 and the second rack 4, the weight of the piston 5b acting to press down the piston 5b, and the differential pressure moving up and down the piston 5b, therefore it is possible to prevent from the moving of the piston 5b.

As shown in FIG. 3, when the piston 5b is pulled up to the top dead position, for example, the cylinder 5a is filled with the specific volume of the sample. The thumb is released from the sucking button 4a, and then the sample suction to the detecting cell and the injector 5 is completed. At this time, since the piston 5b stops when the thumb is released from the sucking button 4a, it is possible to avoid steadily that the sucked sample is discharged from the injector 5 and the detecting cell, and that the air is sucked to the detecting cell after the sample When the sample suction is re-started after suspending for some reason, it is only to re-start pressing the sucking button 4a. And in case of discharging the sample, it is only to press down the discharging button 3a.

When the specific measurement has been carried out after the sample suction, or when the sample suction is suspended for some reason before completing the specific measurement, pressing down the sucking button 3a presses the piston 5b to the side of the port 5d, and then the sample is discharged from the injector via the detecting cell. When the piston 5b is pressed down to the bottom dead position, the entire volume of the sample is discharged from the injector 5, that is, it turns back the state shown in FIG. 2.

Specifically, the sample-suction and discharging apparatus of the invention is arranged to be able to suck the sample into the injector by pressing the sucking button 4a with one finger of hand, and also to be able to discharge the sample from the injector 5 by pressing the discharging button 3a with one finger of the hand, while grasping the injector by the hand. That is to say, the sucking operation and the discharging operation can be performed by one hand; therefore the apparatus has a superior manipulation.

And since the power of the operation can be adjusted according to the viscosity of the sample, it is possible to suck even the high viscosity sample easily. By adjusting the operating speed of the sucking button 4a, it is possible to adjust the suction speed; on the other hand, by adjusting the operating speed of the discharging button 3a, it is possible to adjust the discharging speed. As a result, it becomes possible to control the volume of the sample to be supplied to the detecting cell preciously, and to improve the measurement accuracy.

Figure 4:
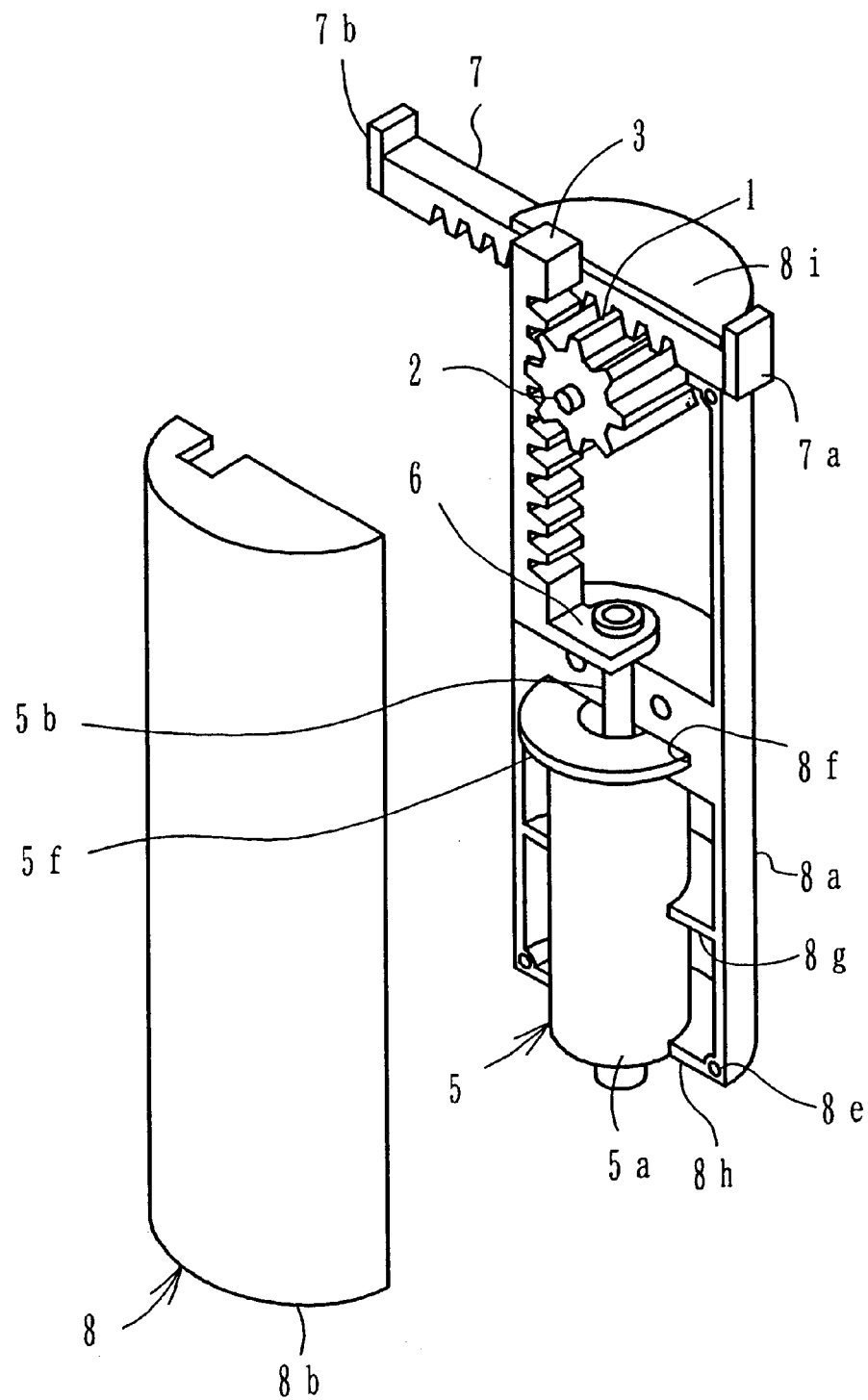
FIG. 4 is an exploded perspective view of the invention.
Figure 5:
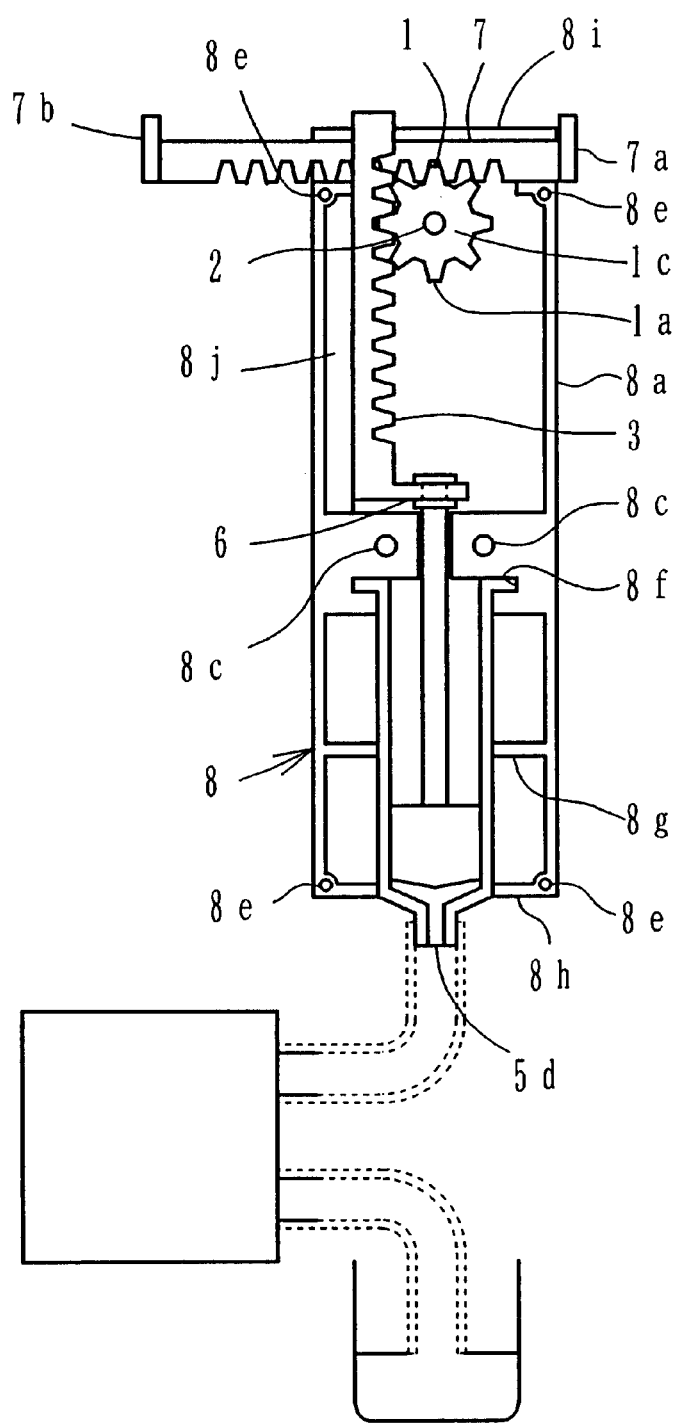
FIG. 5 is a block diagram of the invention.
Figure 6:
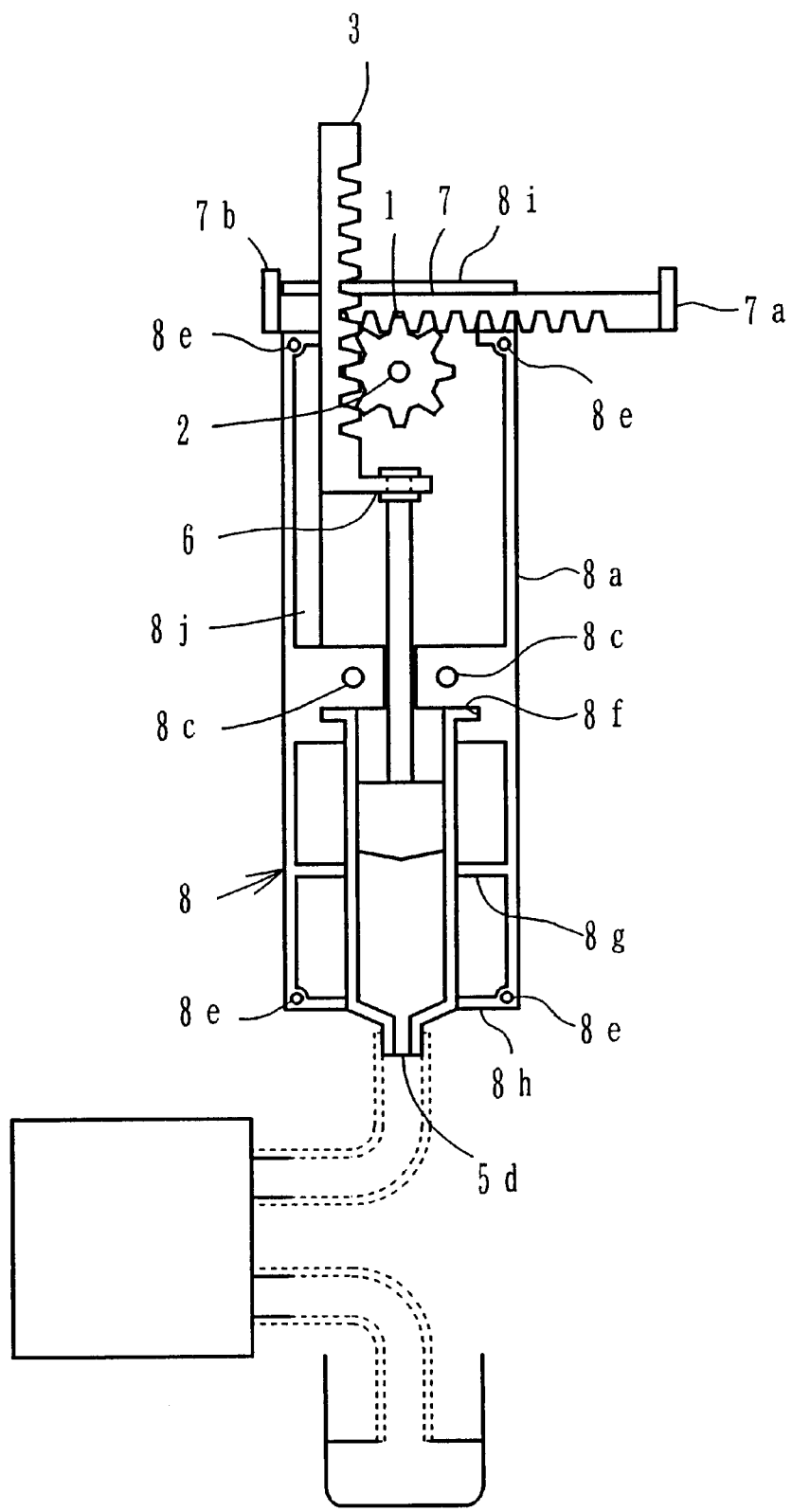
FIG. 6 is a block diagram of the invention.

FIG. 4 shows a perspective view of a sample sucking-discharging device in the invention, and FIG. 5 and FIG. 6 shows block diagrams that indicate schematically the construction of the sample sucking-discharging device. There are different points in the sample sucking-discharging device that a second rack 7 is held in the main body so as to move in the direction crossing the moving direction of the first rack 3, and that a discharging button 7b is provided at one end of the second rack 7 while a sucking button 7a is provided at the other end.

Specifically, as shown in the drawing, the second rack 7 pierces through the main body 8 and is provided so as to slide in the direction crossing in right angles with the shaft 2, and the shaft 2 holds the gear 1 so that the gear 1 can rotate while meshing with the first rack 3 and the second rack. The discharging button 7b is provided at one end of the second rack 7, while the sucking button 7a is provided at the other end.

As shown in FIG. 5, the sample sucking-discharging device in which the piston 5b is positioned at the bottom dead position is grasped with one palm and three fingers except the thumb and the forefinger, after soaking into the sample the sample inlet of the detecting cell connected with the port 5d formed at the bottom end of the cylinder 5a of the injector 5, and under these conditions the thumb presses the sucking button 7b in the right direction. Thereby, the rack 3 and the piston 5b are pulled up via the gear 1, and the sample is sucked into the cylinder 5a. In case of the high viscosity the sample, the sample can be sucked into the cylinder 5a by pressing the sucking button 7b hard, and by adjusting the speed of pressing the sucking button 7b it is possible to adjust the speed of sucking the sample into the cylinder 5a.

At the time of suspending the suction of the sample, the thumb is released from the sucking button 7b. At this time, the rack 7 may stops, therefore it is possible to avoid surely that the piston 5b moves by the sliding resistance of the piston 5b.

When the piston 5b is pulled up to the top dead position as shown in FIG. 6, the cylinder 5a is filled with the specific volume of the sample. By releasing the thumb from the sucking button 7b, the suction of the sample into the injector is completed.

After that, the forefinger presses the discharging button 7a in the left direction, and then the sample in the cylinder 5a is discharged through the sample inlet of the detecting cell. In case of the high viscosity sample, the sample can be discharged from the cylinder 5a by pressing the discharging button 7a hard. Therefore it is possible to adjust the speed of discharging the sample from the cylinder 5a by adjusting the speed of pressing the discharging button 7a.

When the sample supplying is suspended for some reason, the forefinger is released from the discharging button 7a. When releasing the forefinger from the discharging button 7a, the pressing of the rack 3 stops, and the piston 5b will not move by the sliding resistance of the piston 5b. Therefore, it will not occur that the extra sample is supplied from the injector 5 to the detecting cell, or that the sample necessary for the measurement is sucked back from the detecting cell to the injector 5.

In case of proceeding the supplying of the sample, it need to re-start the pressing of the discharging button 7a. When the piston 5b is pressed down to the dead position, the entire volume of the sample is discharged from the injector, and then it turns back to the state shown in FIG. 5.

After completing the measurement of the sample, the sample is discharged from the injector 5 by pressing the discharging button 7a with the thumb.

Specifically, the sample sucking-discharging device in the invention can suck the sample in the injector by pressing the sucking button 7b in the horizontal direction with one finger of hand while grasping the injector 5 with the hand, and also can discharge the sample from the injector 5 by pressing the discharging button 7a in the opposite direction with one finger of the other hand. Therefore, since both the sucking operation and the discharging operation can be performed by one hand, it is possible to improve the manipulation much.

By adjusting the operating power according to the viscosity of the sample, even if the high viscosity sample, the sample can be sucked easily. And by adjusting the operating speed of the sucking button 7b, the speed of the sucking can be adjusted, while by adjusting the operating speed of the discharging button 7a, the speed of the discharging can be adjusted. As a result, since the sample volume to be supplied to the detecting cell can be controlled accurately, it is possible to improve the accuracy of the measurement.

Figure 7:
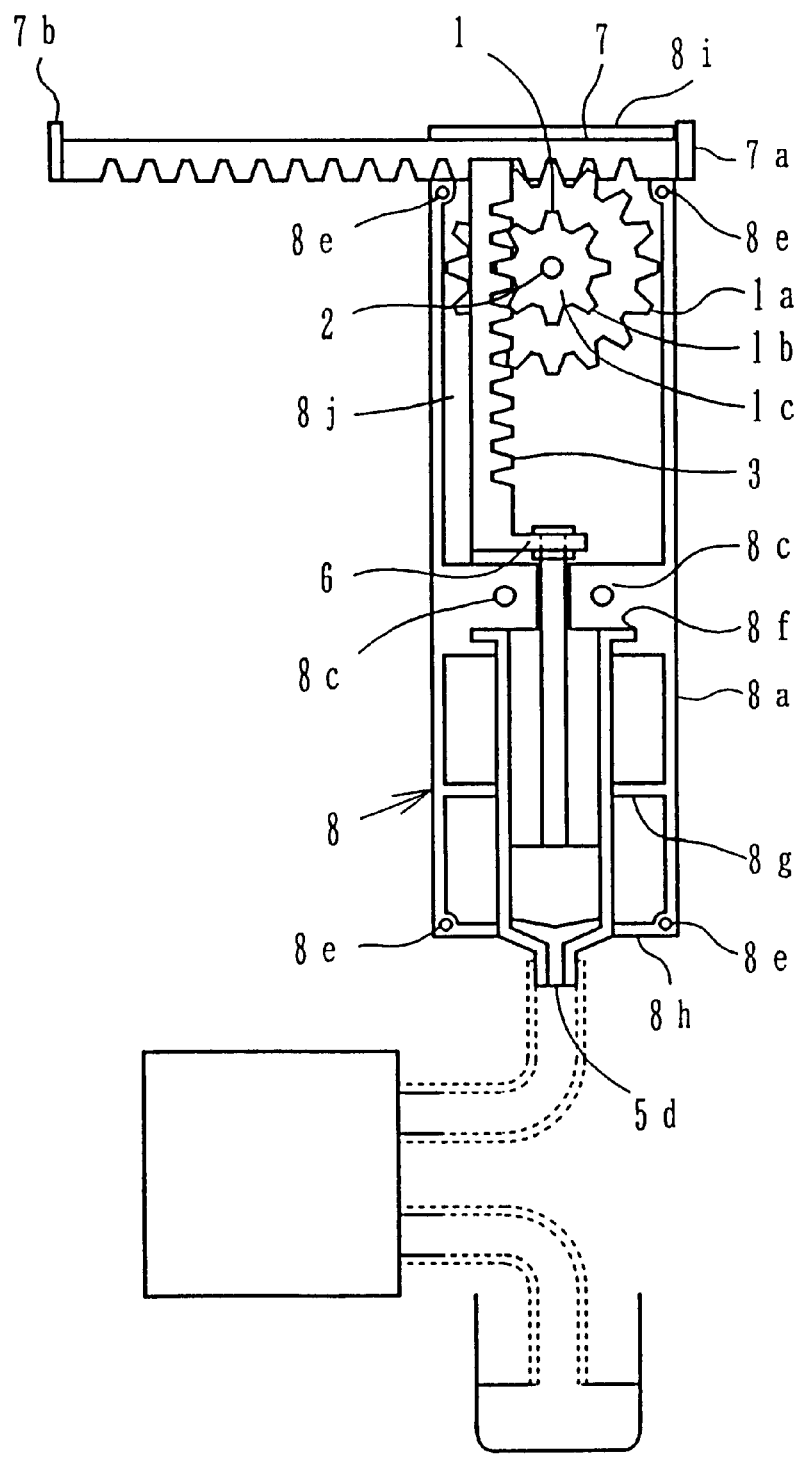
FIG. 7 is a block diagram of the invention.
Figure 8:
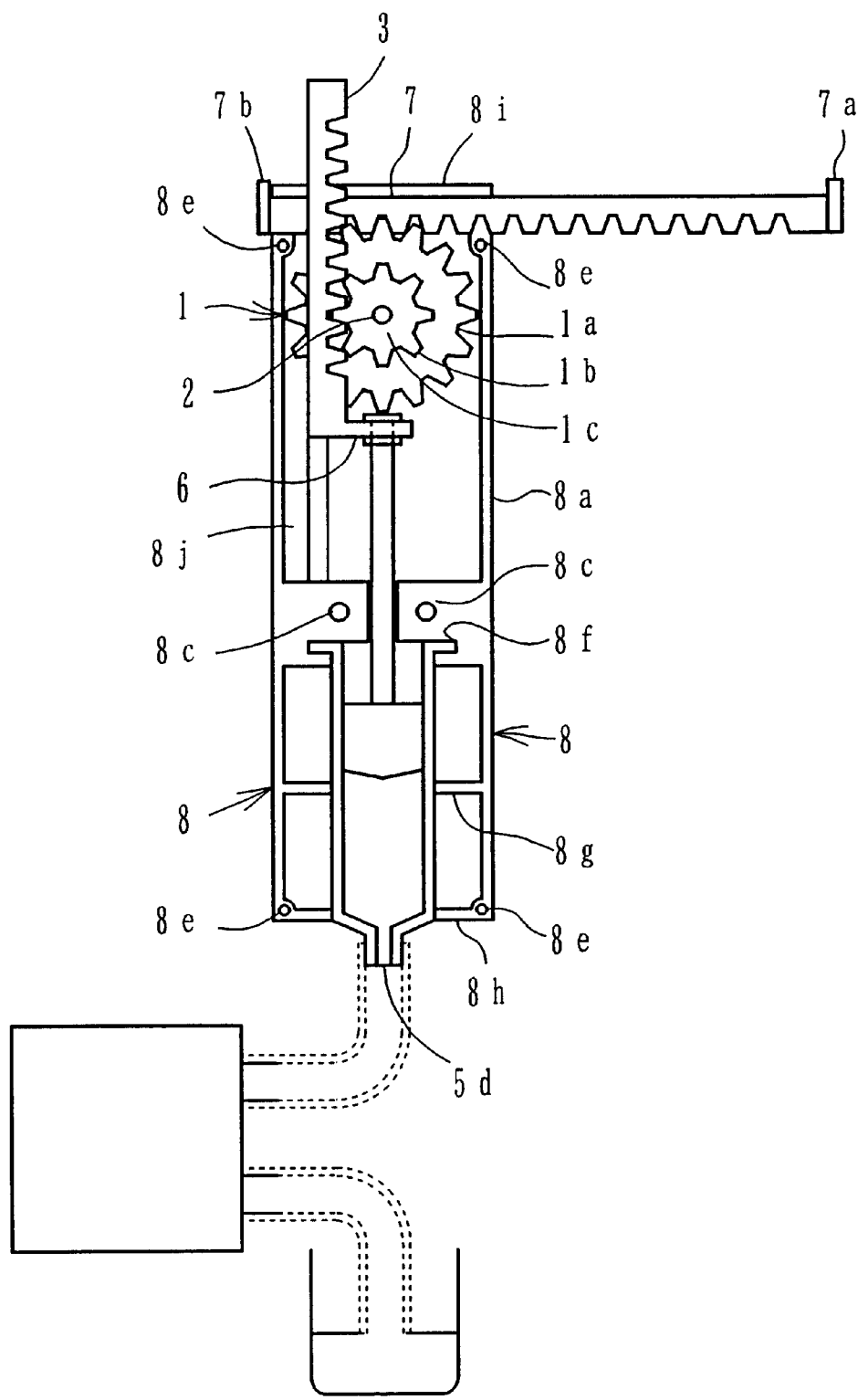
FIG. 8 is a block diagram of the invention.

The other embodiments of the invention shown as each block diagram in FIG. 7 and FIG. 8 adopts a hub 1c and a dual gear provided with teeth line 1a and 1b in large and small radius formed into two lines around the hub 1c as the gear 1. Since the second rack 7 meshes with the teeth line 1a in large radius, and the first rack 3 meshes with the teeth line 1b in small radius respectively, the first rack 3 and the piston 5b can be operated at the half speed of the operation of the second rack 7, and the first rack 3 and the piston 5b can be operated by the twice power of the operation of the second rack 7. Therefore, it becomes easy to perform the fine adjustment of the suction volume of the sample by the small operation power.

And it is possible to obtain the same effect by using a pair of gears comprising large and small gears connected each other instead of the dual gear.

The other constitution, the action and the effect in the embodiment are the same as in the prescribed embodiment, and the explanations are not described here.

Figure 9:
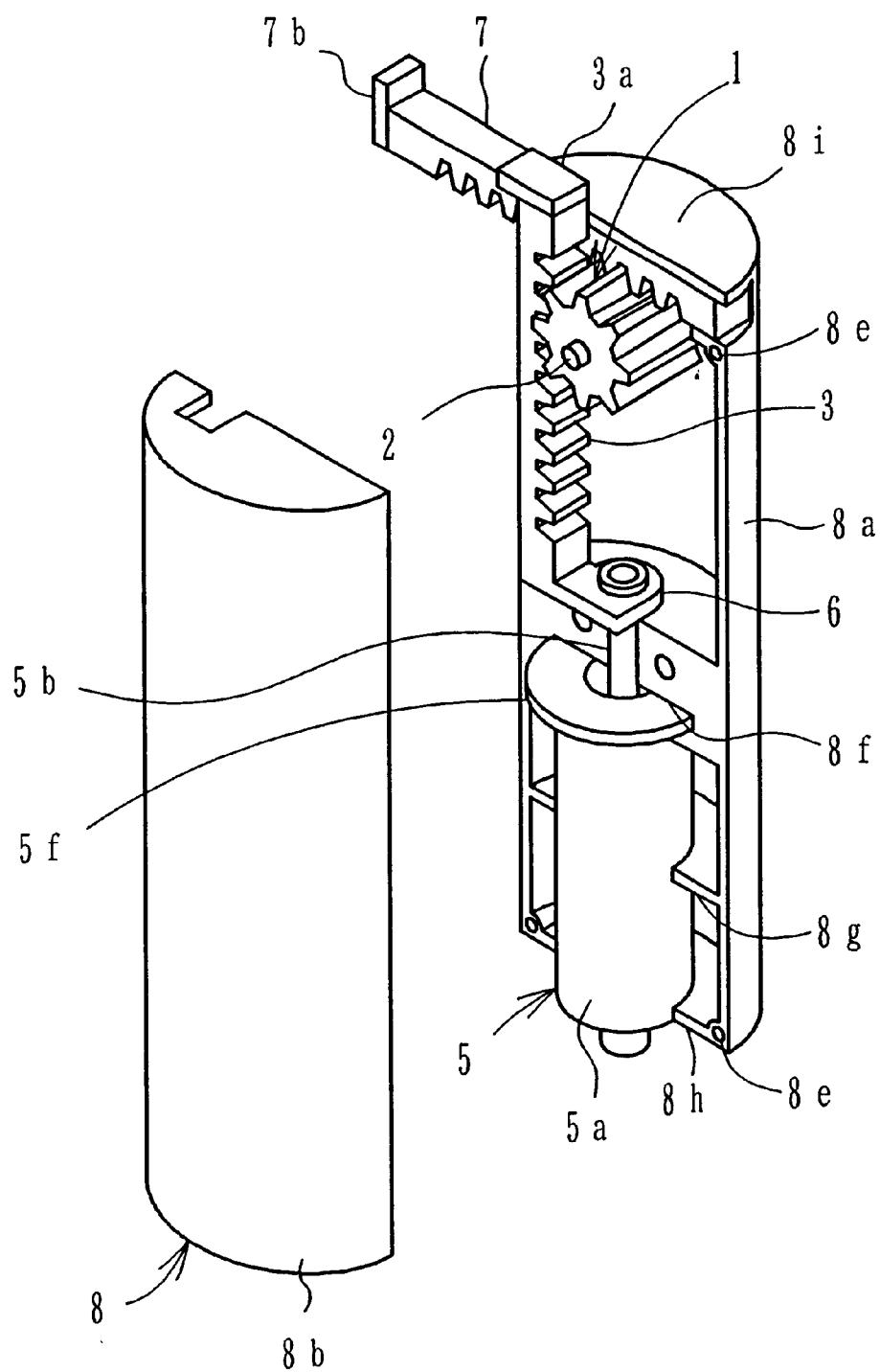
FIG. 9 is an exploded perspective view of the invention.
Figure 10:
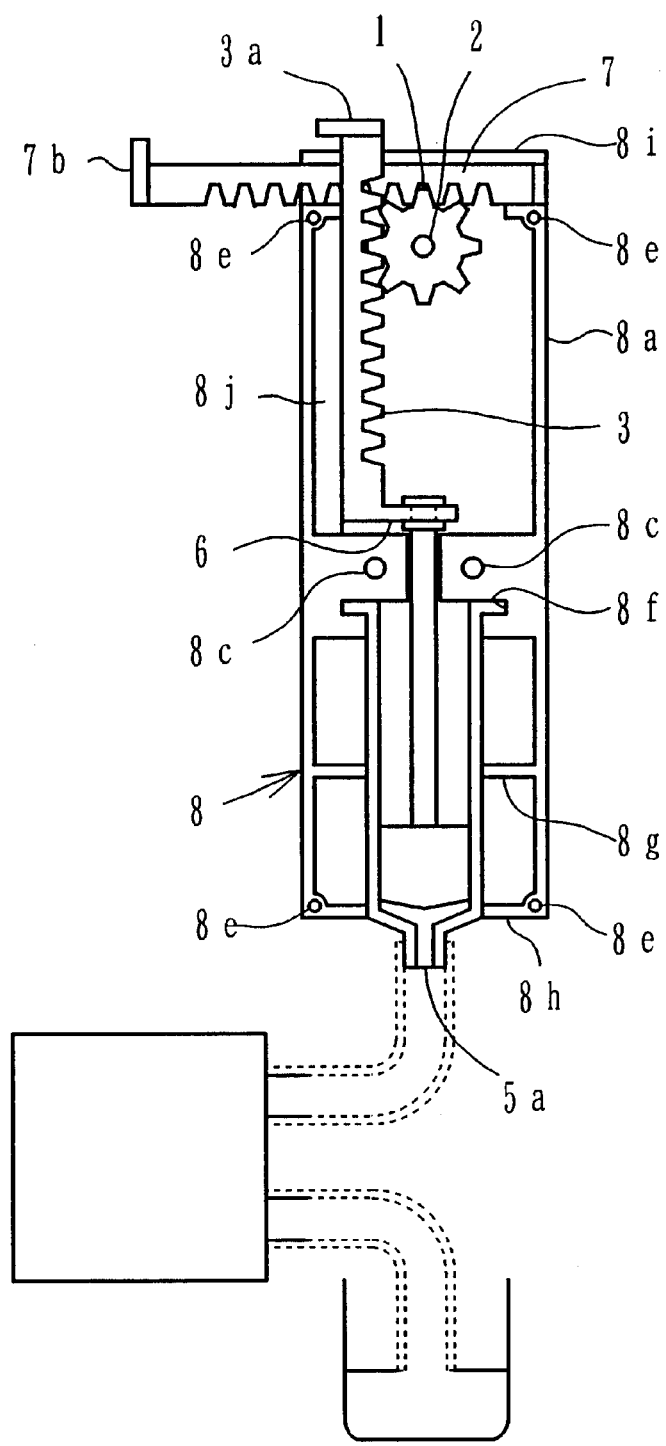
FIG. 10 is a block diagram of the invention.
Figure 11:
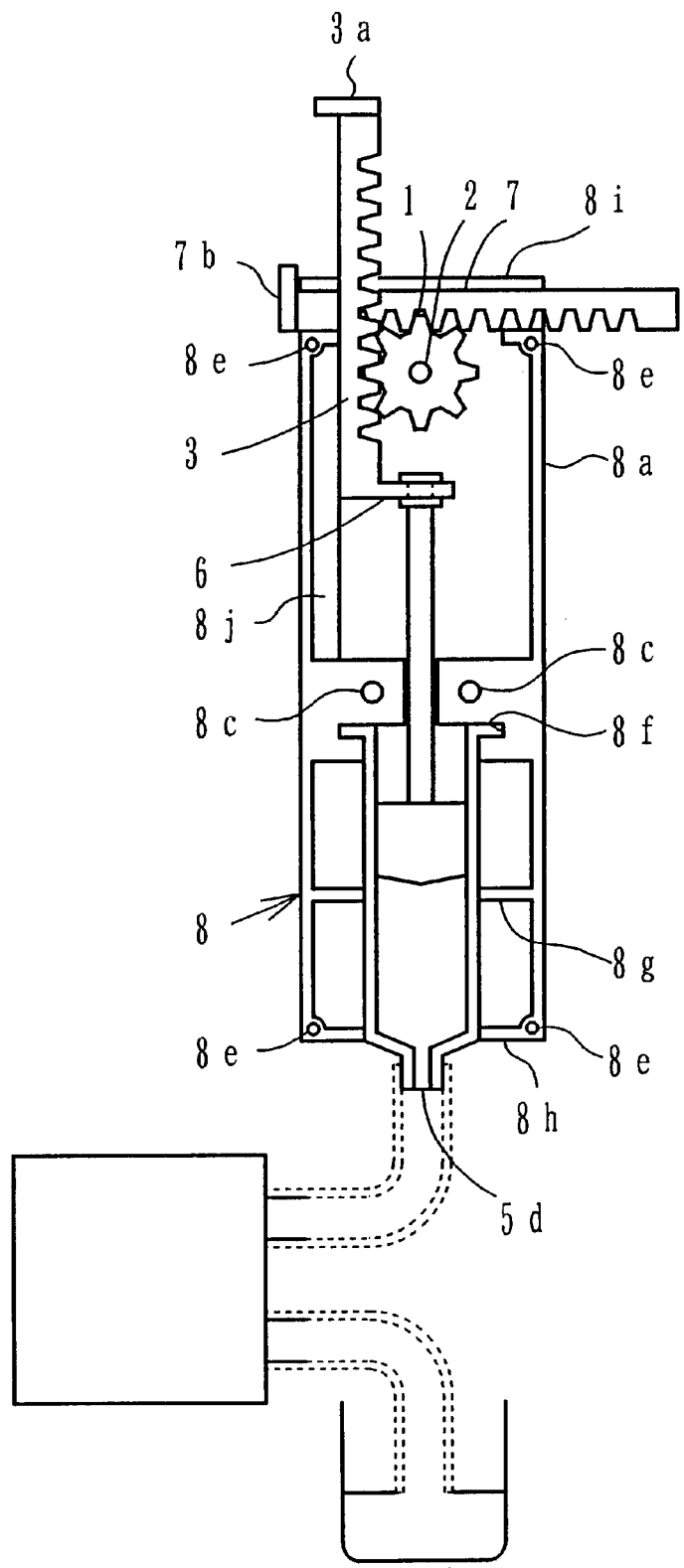
FIG. 11 is a block diagram of the invention.
Figure 12:
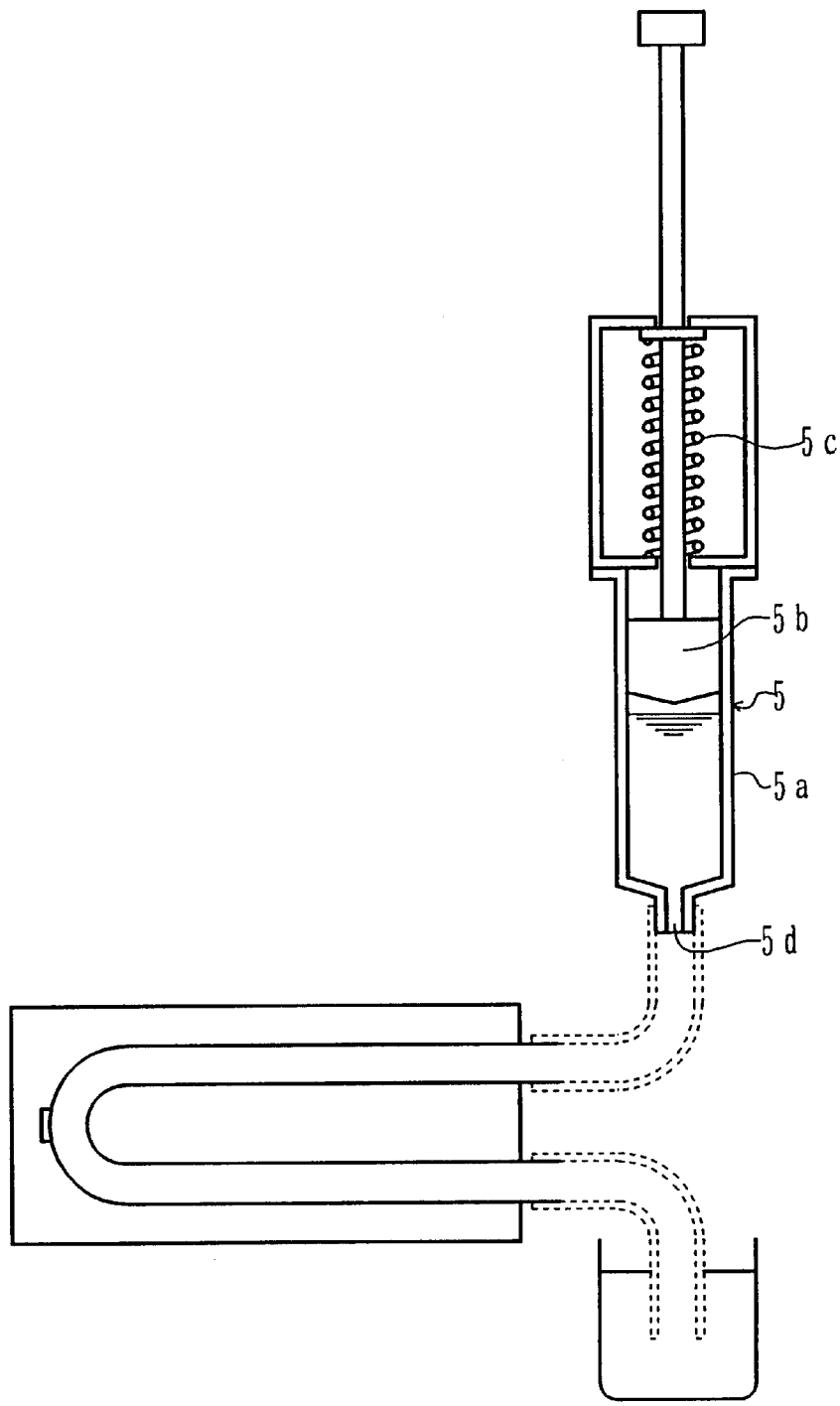
FIG. 12 is a block diagram of the invention.
Figure 13:
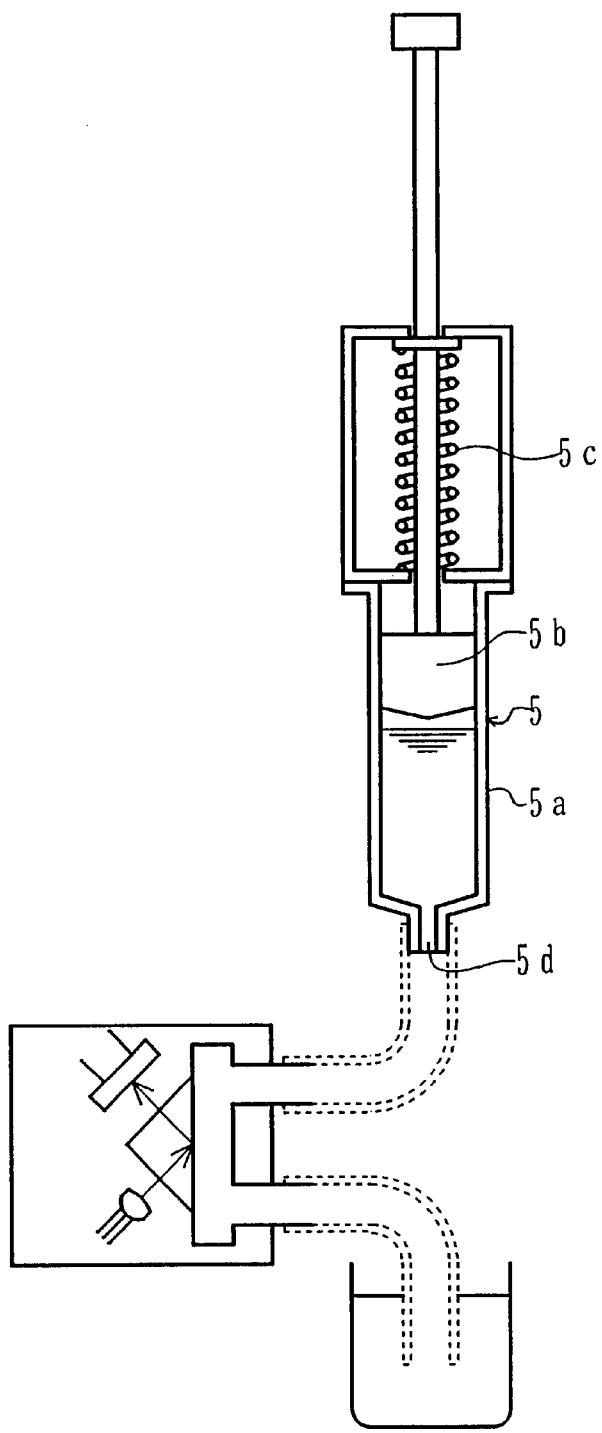
FIG. 13 is a block diagram of the invention.

As shown in the perspective view of FIG. 9 and the block diagrams of FIG. 10 and FIG. 11, the sample sucking-discharging device in the other embodiment of the invention is arranged that the discharging button 3a is provided at the top of the first rack 3 and the sucking button 7b is provided at the end of the second rack 7 moving in the direction crossing in right angles with the moving direction of the first rack 3.

Pressing the sucking button 7b raises the first rack 3 and the piston 5b via the gear 1, and then the sample is sucked in the injector 5. Pressing the discharging button 3a takes down the first rack 3 and the piston 5b, and then the sample is discharged from the injector 5.

The other constitution, the action and the effect in the embodiment are the same as in the prescribed embodiment shown in FIG. 4 to FIG. 6, and the explanations are not described here.

As described above, the sample sucking-discharging device in the invention comprises an injector provided with a cylinder and a piston installed in the cylinder so as to move up and down; a main body for holding the cylinder of the injector; a gear or a pair of gears held in the main body so as to rotate on an axis right-angled to the moving direction of the piston; a first rack, of which one end is connected with the piston, for moving with fitting to the gear or the pair of gears; and, a second rack held in the main body so as to move in the direction opposite to or crossing with the moving direction of the first rack. Thereby, while grasping by one hand the main body of the sample sucking-discharging device in the invention, the finger of the hand presses the rack connected with the piston or the other rack linked with the rack via gear, thereby the sample can be sucked in the injector and discharged from the injector. That is to say, the invention can perform the sample suction to the apparatus and the sample discharge from the apparatus by single hand, so that it is possible to obtain the sample sucking-discharging device with superior manipulation.

And since by pressing with the finger of hand the rack connected with the piston or the other rack linked with the rack via gear while grasping the injector by one hand, the sample can be sucked to the injector and discharged from it, it is possible to suck even the high viscosity sample by adjusting the power of the pressing. And by adjusting the operating speed of the pressing, the speed of sucking and discharging the sample in and out the sample sucking-discharging device can be adjusted. Therefore it is possible to control the suction volume and the supplied volume of the sample to the detecting cell in easy.

And there is no necessity to press the piston or the rack at the time of suspending the suction and discharging, accordingly it is possible to improve the manipulation further more.

What is claimed is:

1. A sample sucking-discharging device comprising an injector provided with a cylinder and a piston installed in the cylinder so as to move up and down; a main body for holding the cylinder of the injector; a gear or a pair of gears held in the main body, wherein each gear comprises a hub, so as to rotate on an axis right-angled to the moving direction of the piston; a first rack, of which one end is connected with the piston, for meshing with the gear or the pair of gears; and a second rack held in the main body so as to move in the direction opposite to or crossing with the moving direction of the first rack wherein the one gear is composed of a dual gear provided with plural teeth formed into two lines on the surrounding of the hub, and the first and the second racks mesh respectively with the lined teeth different from the other.

2. A sample sucking-discharging device comprising an injector provided with a cylinder and a piston installed in the cylinder so as to move up and down; a main body for holding the cylinder of the injector; a gear or a pair of gears held in the main body so as to rotate on an axis right-angled to the moving direction of the piston; a first rack, of which one end is connected with the piston, for meshing with the gear or the pair of gears; and a second rack held in the main body so as to move in the direction opposite to or crossing with the moving direction of the first rack wherein the pair of gears are connected to each other so as to rotate in the same direction synchronously, and the first and the second racks mesh respectively with a different gear of said pair of gears.

3. A sample sucking-discharging device comprising an injector provided with a cylinder and a piston installed in the cylinder so as to move up and down; a main body for holding the cylinder of the injector; a gear or a pair of gears held in the main body so as to rotate on an axis right-angled to the moving direction of the piston; a first rack, of which one end is connected with the piston, for meshing with the gear or the pair of gears; and a second rack held in the main body so as to move in the direction opposite to or crossing with the moving direction of the first rack wherein the second rack is held in the main body so as to move in the direction crossing with the moving direction of the first rack while meshing with the gear or the pair of gears, a discharging button is provided at one end of the second rack and a sucking button at the other end of the second rack, thereby pressing the discharging button presses down the piston to the bottom of the cylinder via the second rack, the gear or the pair of gears, and the first rack; and, pressing the sucking button pulls up the piston to the upper side of the cylinder via the second rack, the gear or the pair of gears, and the first rack.

4. A sample sucking-discharging device according to claim 3, comprising a gear composed of dual gear provided with teeth in a different radius formed into two lines, wherein a gear in small radius is meshed with the first rack, while a gear in large radius is meshed with the second rack.

5. A sample sucking-discharging device according to claim 3, comprising a pair of gears in a different radius, wherein a gear in small radius is meshed with the first rack, while a gear in large radius is meshed with the second rack.

6. A sample sucking-discharging device according to claim 3, wherein the one gear is provided with a hub and a plurality of teeth lined on the surrounding of the hub, and the first and the second rack mesh with the lined teeth.

7. A sample sucking-discharging device comprising an injector provided with a cylinder and a piston installed in the cylinder so as to move up and down; a main body for holding the cylinder of the injector; a gear or a pair of gears held in the main body so as to rotate on an axis right-angled to the moving direction of the piston; a first rack, of which one end is connected with the piston, for meshing with the gear or the pair of gears; and a second rack held in the main body so as to move in the direction opposite to or crossing with the moving direction of the first rack wherein the second rack is held in the main body so as to move in the direction crossing with the moving direction of the first rack while meshing with the gear or the pair of gears, a discharging button is provided at one end of the first rack, the other end of which is connected with a piston, and a sucking button is provided at one end of the second rack, thereby pressing the discharging button presses down the piston to the bottom of the cylinder via the first rack; and on the other hand, pressing the sucking button pulls up the piston to the upper side of the cylinder via the second rack, the gear or the pair of gears, and the first rack.

* * * * *